US00PP19072P2

(12) United States Plant Patent
Egger

(10) Patent No.: US PP19,072 P2
(45) Date of Patent: Aug. 5, 2008

(54) ***HEUCHERA* PLANT NAMED 'MAHOGANY'**

(50) Latin Name: *Heuchera hybrida*
Varietal Denomination: Mahogany

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/879,447

(22) Filed: Jul. 16, 2007

(51) Int. Cl.
*A01H 5/00* (2006.01)

(52) U.S. Cl. ..... Plt./440
(58) Field of Classification Search ..... Plt./440
See application file for complete search history.

*Primary Examiner*—Kent L. Bell
*Assistant Examiner*—June Hwu
(74) *Attorney, Agent, or Firm*—Klarquist Sparkman LLP

(57) ABSTRACT

A new and distinct *Heuchera* plant substantially as shown and described, characterized by shiny, ruffled, red-brown leaves and good vigor.

1 Drawing Sheet

Botanical denomination: *Heuchera hybrida.*
Variety designation: 'Mahogany'.

BACKGROUND OF THE INVENTION

The present invention relates to a new and distinct cultivar of *Heuchera hybrida* and given the cultivar name of 'Mahogany'. *Heuchera* is in the family Saxifragaceae. *Heuchera* 'Mahogany' originated from a cross between *Heuchera* 123-1 (a proprietary unreleased plant), as the seed parent, and *Heuchera* 148-10 (a proprietary unreleased plant), as the pollen parent. Given its ornamental foliage and flower form it is probable that *Heuchera micrantha, H. americana, H. brizoides,* and *H. sanguinea* are in its parentage.

SUMMARY OF THE INVENTION

This new *Heuchera* is distinguished by:

1. Shiny, red-brown, ruffled leaves.
2. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
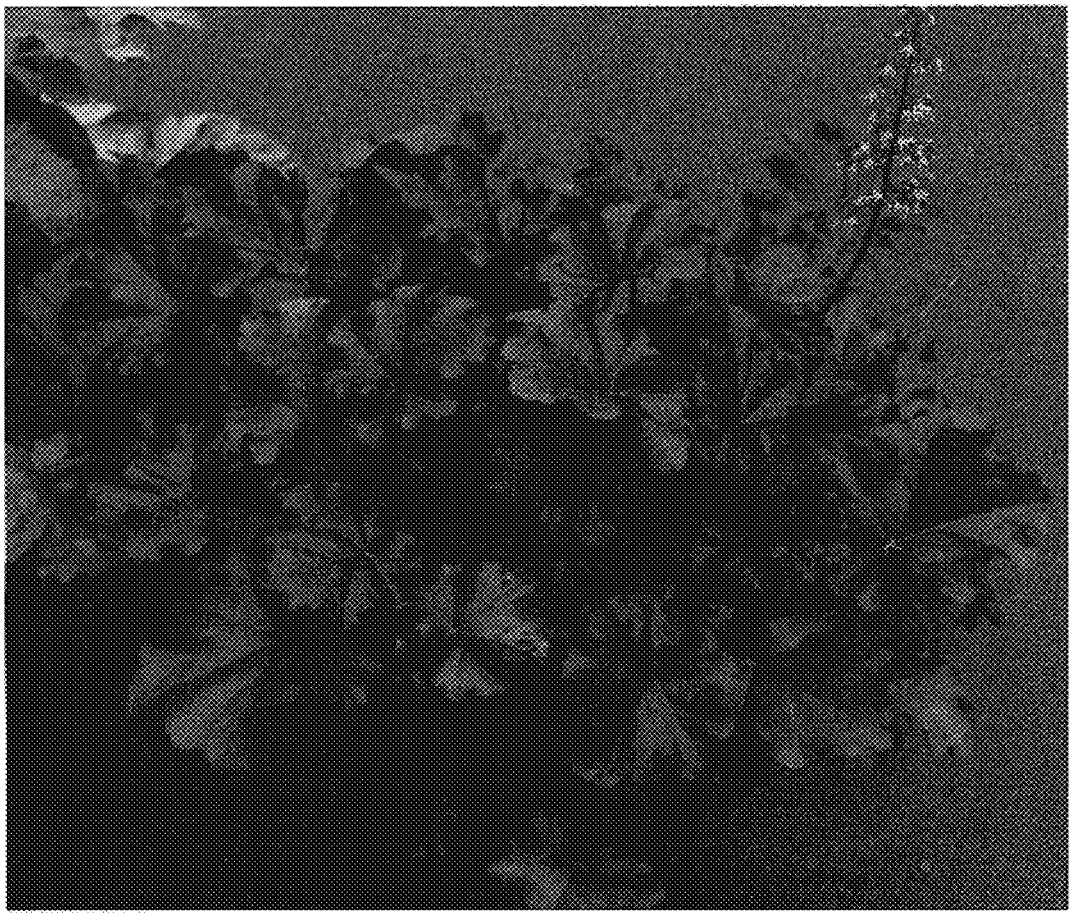
FIG. 1 shows a two year old *Heuchera* 'Mahogany' in bloom, growing in a one gallon container in the shade house in late spring in Canby, Oreg.
Figure 2:
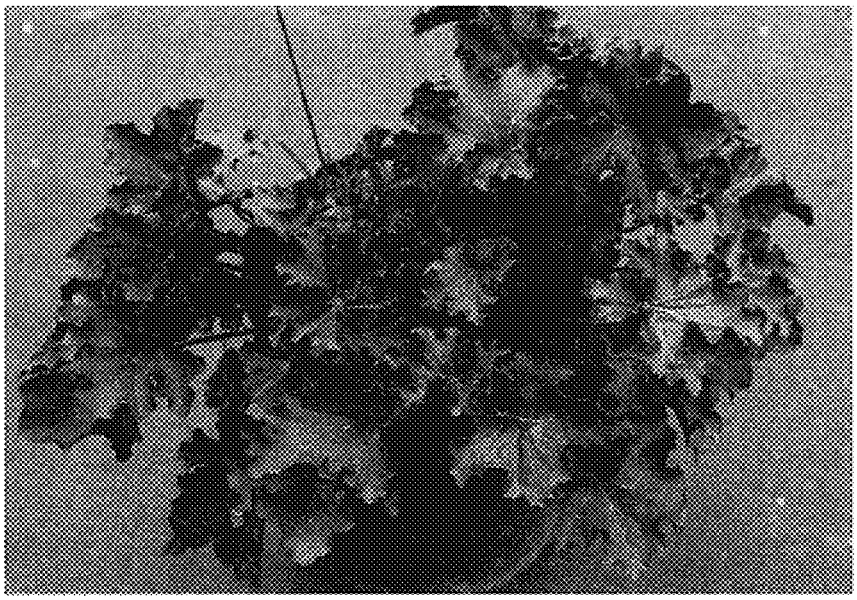
FIG. 2 shows a one year old *Heuchera* 'Mahogany' in a one gallon container grown outside all winter in early March in Canby, Oreg.

The following is a detailed description of the new *Heuchera* cultivar based on observations of a one-year-old specimen grown in a 1 gallon container in a cool greenhouse in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—20 cm tall from top of the foliage to the ground and 35 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Rosette.
*Shape.*—Broadly ovate.
*Lobing/division.*—5 main lobes, with 2 to 3 shallow secondary lobes.
*Venation.*—Palmate.
*Margins.*—Crenate and undulate.
*Apex.*—Mucronulate.
*Base.*—Cordate, lobes overlapping at the base.
*Blade size.*—5 to 7 cm long and 5 to 7.5 cm wide.
*Surface texture.*—Sparsely glandular both sides.
*Texture.*—Thin, leathery.
*Petiole description.*—6 to 12 cm long and 2 mm wide, glandular hairs. Greyed Purple 187C.
*Leaf color.*—Spring, topside Greyed Orange 177A darkening to between Greyed Purple 187B and Brown 200B, bottom side Red Purple 59A; summer, fall topside, Greyed Purple 183A, bottom side between Greyed Purple 187A and Red Purple 59A; winter topside Greyed Purple 187A, bottom side between Greyed Purple 187A and Red Purple 59A.

Inflorescence:

*Size.*—5 to 7 cm wide and 12 to 17 cm long.

*Type.*—Thyrse.

*Number of flowers per thyrse.*—45 to 75 per thyrse.

*Number of thyrse.*—15 in spring bloom.

*Peduncle.*—About 35 cm tall, 3 to 4 mm wide at base, Greyed Purple 187A, glandular hairs, with 2 to 4 petiolate cauline leaves (ovate to broadly ovate, blades 3 to 6 cm long and 2 to 6 cm wide with a lobed and crenate margin, color between Greyed Purple 187B and Brown 200B).

*Pedicel.*—Variable in size, with glandular hairs, Greyed Purple 187A.

*Bloom period.*—Late April to June in Canby, Oreg.

Flower bud:

*Size.*—2.5 mm wide and 3 mm long.

*Description.*—Glandular puberulent, ovoid.

*Color.*—Top quarter is Greyed Orange 174A, bottom three quarters is Yellow Green 153B.

Flower:

*Type.*—Perfect, male sterile.

*Shape.*—Campanulate.

*Size.*—5 mm long and 4 mm wide.

*Petal description.*—5 in number, inconspicuous, 2 mm long, spatulate with a clawed base, reflexed, tip obtuse, margin entire, glandular on both sides, White 155A on top side and Red Purple 69B on the bottom side.

*Calyx description.*—3 mm long and 4 mm wide, with 5 lobes, divided ⅓ way to the base, glandular hairs on both sides, tip acute, margin entire, Greyed Yellow 153A on the top half and Greyed Orange 172B on the bottom half, on both sides.

*Stamen description.*—5 in number, 1.5 mm long, filament 5 mm long, Yellow Green 145D, anther 1 mm long, Greyed Orange 177A.

*Pistil description.*—One central two beaked pistil, 5 mm long, Greyed Yellow 160D overall, ovary 2 mm long, each style 3 mm long.

*Fragrance.*—None.

*Lastingness.*—Each thyrse blooms for about 2 weeks on the plant.

Fruit:

*Type.*—Two beaked capsule.

*Size.*—7 mm deep by 2 mm wide.

*Fertility.*—Good.

*Color.*—Greyed Red 182A.

Seed:

*Shape.*—Linear.

*Size.*—2 mm long.

*Color.*—Black, RHS 202A.

Disease and pest tolerance: No known resistance to rust, a common problem with light leaf type *Heuchera*. Excellent disease tolerance to powdery mildew. All *Heuchera* are susceptible to root weevils.

COMPARISON TO SIMILAR *HEUCHERA*

Compared to *Heuchera* 'Black Beauty' (U.S. Plant Pat. No. 13,288), this new variety has lighter colored foliage, between deep maroon and dark brown, rather than between deep maroon and black. The new variety has edges that are rounded or less sharply cut.

Compared to the seed parent, *Heuchera* 123-1, the new variety has red-brown rather than purple-black colored leaves and ruffled rather than unruffled leaves.

Compared to the pollen parent, *Heuchera* 148-10, the new variety has red-brown rather than pinkish-amber colored leaves.

I claim:

1. A new and distinct *Heuchera* plant as herein illustrated and described.

* * * * *